(12) United States Patent
Foote et al.

(10) Patent No.: US 11,439,718 B2
(45) Date of Patent: Sep. 13, 2022

(54) IV POLE ISOLATION AND CLEANING DEVICES AND METHODS

(71) Applicant: Merit Medical Systems, Inc., South Jordan, UT (US)

(72) Inventors: Kirk Loren Foote, Cottonwood Heights, UT (US); Mahender Avula, San Diego, CA (US); Jim Mottola, West Jordan, UT (US); Richard P. Jenkins, Bluffdale, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 190 days.

(21) Appl. No.: 16/743,928

(22) Filed: Jan. 15, 2020

(65) Prior Publication Data

US 2020/0230272 A1 Jul. 23, 2020

Related U.S. Application Data

(60) Provisional application No. 62/794,186, filed on Jan. 18, 2019.

(51) Int. Cl.
*A61L 2/10* (2006.01)
*A61L 2/08* (2006.01)
*A61L 2/26* (2006.01)

(52) U.S. Cl.
CPC .............. *A61L 2/10* (2013.01); *A61L 2/088* (2013.01); *A61L 2/26* (2013.01); *A61L 2202/11* (2013.01); *A61L 2202/14* (2013.01); *A61L 2202/16* (2013.01); *A61L 2202/24* (2013.01)

(58) Field of Classification Search
CPC ... A61L 2/10; A61L 2/088; A61L 2/26; A61L 2202/11; A61L 2202/14; A61L 2202/16; A61L 2202/24
See application file for complete search history.

(56) References Cited

U.S. PATENT DOCUMENTS

| | | | |
|---|---|---|---|
| 4,723,912 A | 2/1988 | Nieusma | |
| 5,069,907 A | 12/1991 | Mixon et al. | |
| 5,078,483 A | 1/1992 | Herzberg | |
| 7,598,501 B2 | 10/2009 | Jones | |
| 2008/0006278 A1 | 1/2008 | Henke-Sarmento et al. | |

(Continued)

FOREIGN PATENT DOCUMENTS

| | | |
|---|---|---|
| JP | 2016039846 | 3/2016 |
| KR | 101207286 | 12/2012 |

(Continued)

OTHER PUBLICATIONS

European Search Report dated Mar. 5, 2021 for EP18806566.8.

(Continued)

*Primary Examiner* — Sean E Conley
(74) *Attorney, Agent, or Firm* — Dorsey & Whitney LLP

(57) ABSTRACT

Devices and methods to disinfect a medical appliance, such as an IV pole, using ultraviolet light, including ultraviolet C (UVC) light, are disclosed. The devices and methods expose contaminated exterior surfaces of the IV pole to UVC light. The UVC light may be emitted from within the IV pole or may be emitted from a source surrounding the IV pole. A controller controls the duration and intensity of the exposure. A proximity sensor detects the proximity of a healthcare worker or patient.

13 Claims, 7 Drawing Sheets

(56) References Cited

U.S. PATENT DOCUMENTS

| | | | |
|---|---|---|---|
| 2008/0193496 A1 | 8/2008 | Gabbay | |
| 2009/0065067 A1 | 3/2009 | Bushman et al. | |
| 2011/0309268 A1 | 12/2011 | Parker | |
| 2015/0090903 A1* | 4/2015 | Cole | A61L 2/24 250/492.1 |
| 2015/0335774 A1* | 11/2015 | Gomez | A61L 2/10 250/454.11 |
| 2018/0178823 A1 | 6/2018 | Yang et al. | |
| 2018/0338810 A1 | 11/2018 | Lampropoulos et al. | |
| 2020/0188543 A1* | 6/2020 | Etter | A61B 50/22 |

FOREIGN PATENT DOCUMENTS

| | | |
|---|---|---|
| KR | 1020120140564 | 12/2012 |
| KR | 1020120140566 | 12/2012 |
| KR | 101590163 | 1/2016 |
| KR | 1020160132899 | 11/2016 |
| WO | 2004016299 | 2/2004 |
| WO | 2017015207 | 1/2017 |

OTHER PUBLICATIONS

International Search Report and Written Opinion dated Sep. 17, 2018 for PCT/US2018/034466.
"Puro—Processing Health and Promoting Wellness Through Light", Brochure, 2019.
International Search Report and Written Opinion dated May 7, 2020 for PCT/US2020/013728.
Office Action dated Jul. 2, 2020 for U.S. Appl. No. 15/988,923.

* cited by examiner

IV POLE ISOLATION AND CLEANING DEVICES AND METHODS

RELATED CASES

This application claims priority to U.S. Provisional Application No. 62/794,186, filed on Jan. 18, 2019, and titled "IV Isolation and Cleaning Devices and Methods," which is hereby incorporated by reference in its entirety.

TECHNICAL FIELD

The present disclosure relates generally to medical devices. More specifically, the present disclosure relates to devices and methods to disinfect a medical appliance, such as an IV pole, using ultraviolet (UV) light.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings, in which:

DETAILED DESCRIPTION

Figure 1:
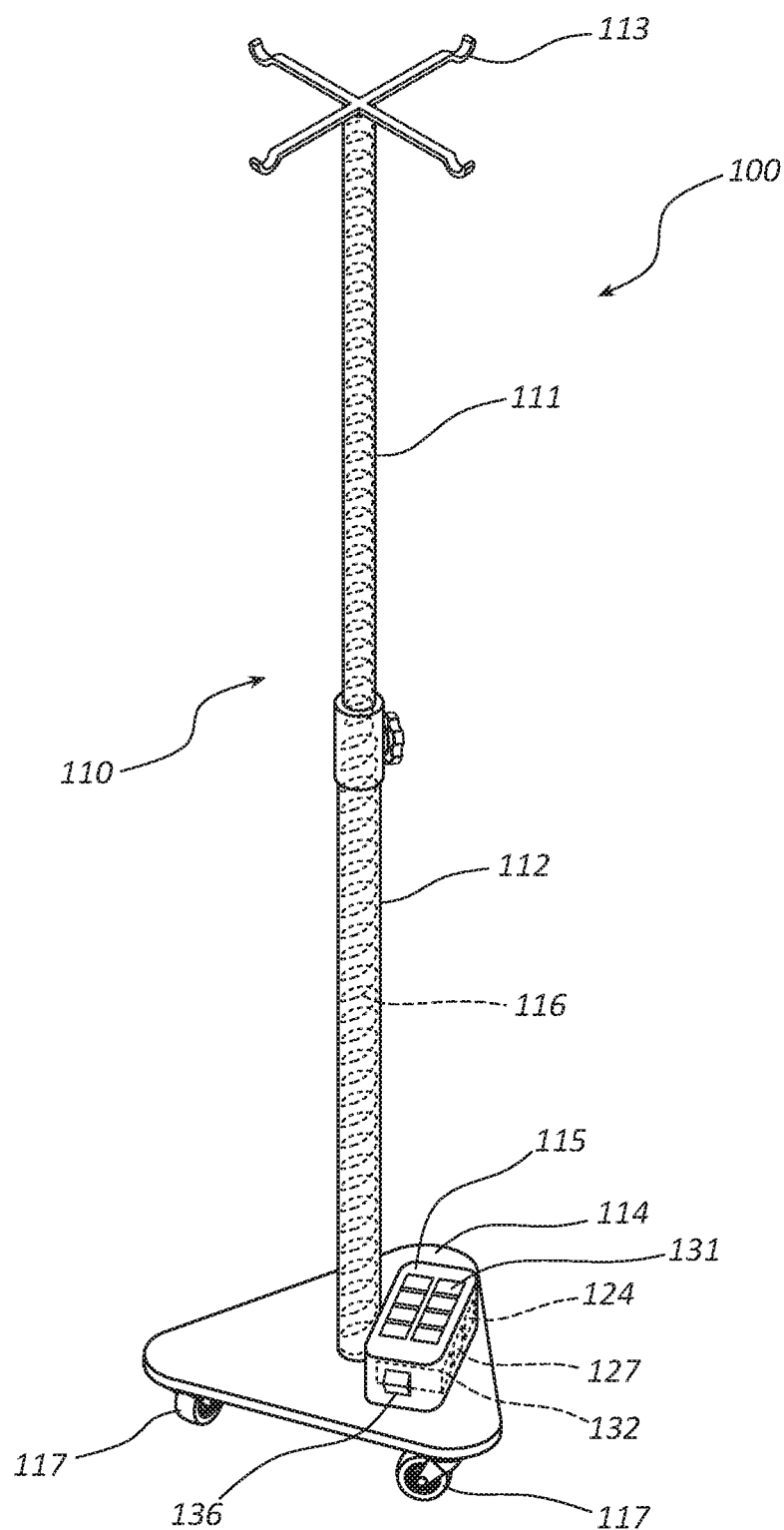
FIG. 1 is a perspective view of a UV disinfecting device coupled to an IV pole.

Nosocomial infections are a major cause of morbidity and mortality in hospitals and other clinical settings. In certain instances, the source of the nosocomial infection may be a cross-contamination from a contaminated medical appliance transferred to a susceptible patient. Medical appliances, such as IV poles, are commonly utilized in hospitals and other clinical environments to support the treatment of patients. A medical appliance may be contaminated by body fluids from one patient, which may be transferred to a second patient. The transfer of contaminants may occur when a medical worker touches a contaminated medical appliance and then touches a patient. Prevention of nosocomial infections is an effort of hospitals and other healthcare providers.

In certain instances, UV light, including ultraviolet C (UVC) light, has been may be utilized as a disinfection agent. UV light makes up a portion of the electromagnetic spectrum between X-rays and visible light. UV light wavelengths span from 10 nm to 400 nm. UVC light wavelengths span from 100 nm to 280 nm. UVC light may be considered "germicidal UV" and various wavelengths may be utilized, including a wavelength of 265 nm. UVC light may be germicidal to bacteria, viruses and other microorganisms when it is absorbed by the DNA and RNA of microorganisms. In some instances, the UVC causes changes to the DNA and RNA structure, rendering the microorganisms incapable of replicating.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

As used herein, an IV pole refers to a structure, including freestanding structures and supported structures, configured to support medical devices, including medicaments configured for intravenous (IV) introduction into a patient. Disclosure set forth herein relating to disinfecting portions of an IV pole may analogously be applied to other medical structures and devices, such as bed rails, wall mounted support rails, cart handles, and so forth.

FIGS. 1-7 illustrate different views of UV disinfecting devices for IV poles. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 is a view of an embodiment of a UV disinfecting device 100. As shown, the UV disinfecting device 100 includes an IV pole 110, a controller 115, and a UV light transmitting member 116. The IV pole 110 may include an upper tube 111, a lower tube 112, a base 114, and a support 113. The upper tube 111 and the lower tube 112 may be formed as hollow, elongate cylinders having a circular cross-section. In some embodiments, the upper tube 111 and the lower tube 112 may be hollow, elongate tubes having other geometric cross-sectional shapes, such as triangular, square, rectangular, or any other suitable polygonal shape. The upper tube 111 may be configured to telescopingly slide within the lower tube 112 to adjust a height of the IV pole 110. The lower tube 112 may be fixedly coupled to the base 114 such that the lower tube 112 extends orthogonally upward from the base 114. The support 113 may be fixedly coupled to an upper end of the upper tube 111. In other embodiments, the support 113 may be removably coupled to the upper tube 111. The base 114 may comprise wheels or castors 117 such that the IV pole 110 may be easily moved by a patient or healthcare worker. The upper tube 111 and the lower tube 112 may be formed from a UVC light transparent material with a transmission cutoff of wavelengths less than 200 nm, such as quartz glass. In other embodiments, the upper tube 111 and the lower tube 112 may be formed from other glass type or polymeric materials, such as cyclic olefin copolymer, fluorinated ethylene propylene (FEP), fused silica, and so forth.

Photobiocidal nanoparticles may be coated or frosted on an outer surface of the upper and lower tubes 111, 112. The photobiocidal nanoparticles may comprise titanium dioxide, silica dioxide, zinc dioxide, or any other suitable photobiocidal material. The photobiocidal nanoparticles may be activated by the UVC light transmitted through walls of the upper and lower tubes 111, 112 from the UV light transmitting member 116. The photobiocidal nanoparticles are configured to enhance the disinfecting properties of the UV disinfecting device 100.

In some embodiments, the upper tube 111 and the lower tube 112 may comprise an antimicrobial, antifungal, and/or antiviral compound. The compound may be incorporated into the material used to form the upper and lower tubes 111, 112, or the compound may be applied to an outer surface as a coating or frosting. In some embodiments, the compound is in a concentration of from 1% to 4%. The compound may comprise agents such as ionic silver; zinc; copper; phenolic biocides; thiabendazole; quaternary ammonium compounds, including quaternary ammonium chlorides such as N,N-didecyl-N,N-diethyl ammonium chloride, and aromatic moieties (Benzalkonium chloride) such as N-decyl-N-benzyl-N,N-dimethylammonium chloride; and so forth. These compounds may be utilized individually or in any combination to enhance antimicrobial properties of the IV pole 110.

With continued reference to FIG. 1, in the illustrated embodiment, the controller 115 is coupled to the base 114. In other embodiments, the controller 115 may be coupled to either the upper tube 111 or the lower tube 112 of the IV pole 110. The controller 115 may include a power supply 132, a processor 127, a UVC light emitting member 124, and a proximity sensor 136. The power supply 132 may comprise rechargeable batteries. Alternatively or additionally, a power cord from an electrical outlet or other electrical power source may be plugged into the power supply 132 to recharge the batteries and may be unplugged from the power supply 132 when the UV disinfecting device 100 is moved.

The UVC light emitting member 124 may be configured to output UV light, such as UVC light, to the UV light transmitting member 116 including light along a wavelength spectrum of from 200 nm to 300 nm, from 250 nm to 280 nm, from 260 nm to 270 nm, and at 265 nm. The UVC light emitting member 124 may comprise a variety of sources, including a mercury-based lamp, a UV light emitting diode, and a pulsed-xenon lamp. The processor 127 may be configured to control duty cycles of the UVC light emitting member 124. For example, the processor 127 may control the frequency, duration, and intensity at which the UVC light emitting member 124 produces UVC light. For example, the processor 127 may be programmed to activate the UVC light emitting member 124 following a period of use of the UV disinfecting device 100. The activation period may be programmed to exceed a minimum UVC light exposer requirement of 16,000 microwatt seconds per $cm^2$ to achieve disinfection of the IV pole 110. The proximity sensor 136 may be coupled to the processor 127 and may be configured to sense the proximity of the patient or the healthcare worker, and a signal may be sent to the processor 127 such that the UVC light emitting member 124 is turned off or not permitted to start emitting UVC light. (UVC light is harmful to soft tissues such as skin and eyes and a proximity sensor may thus be configured as a safety feature.) The controller 115 may comprise LED lights 131 to visibly indicate the status of the controller 115, such as on, off, charging, low battery, etc.

In the illustrated embodiment, the UV light transmitting member 116 is coupled to the controller 115. The UV light transmitting member 116 may comprise an optical cable or any other suitable structure configured to transmit UV light and, more particularly, UVC light. The UV light transmitting member 116 is disposed within the upper and lower tubes 111, 112. The UV light transmitting member 116 may be disposed in a spiral configuration to maximize the length of the UV light transmitting member 116 disposed within the upper and lower tubes 111, 112. In other embodiments, the UV light transmitting member 116 may be straight or divided into a plurality of strands.

In use, the UV disinfecting device 100 may be used in a healthcare setting to hang medicament bags from the support 113 when providing medical treatment to the patient. The upper and lower tubes 111, 112 may be handled by the patient or healthcare worker to move the UV disinfecting device 100 to an acceptable location. Handling of the UV disinfecting device may contaminate the outer surface of the upper and lower tubes 111, 112 with pathogenic microorganisms. Following the patient treatment, the UV disinfecting device 100 may be disinfected to avoid cross-contamination of the pathogenic microorganisms to a second patient. The UVC light emitting member 124 can emit UVC light to the UV light transmitting member 116. The UV light transmitting member 116 may transmit the UVC light through a wall of the upper and lower tubes 111, 112. The UVC light may kill or disable the microorganisms disposed on the outer surface of the upper and lower tubes 111, 112. The UVC light may also activate the photobiocidal nanoparticles to enhance the killing or disabling of the microorganisms.

Figure 2:
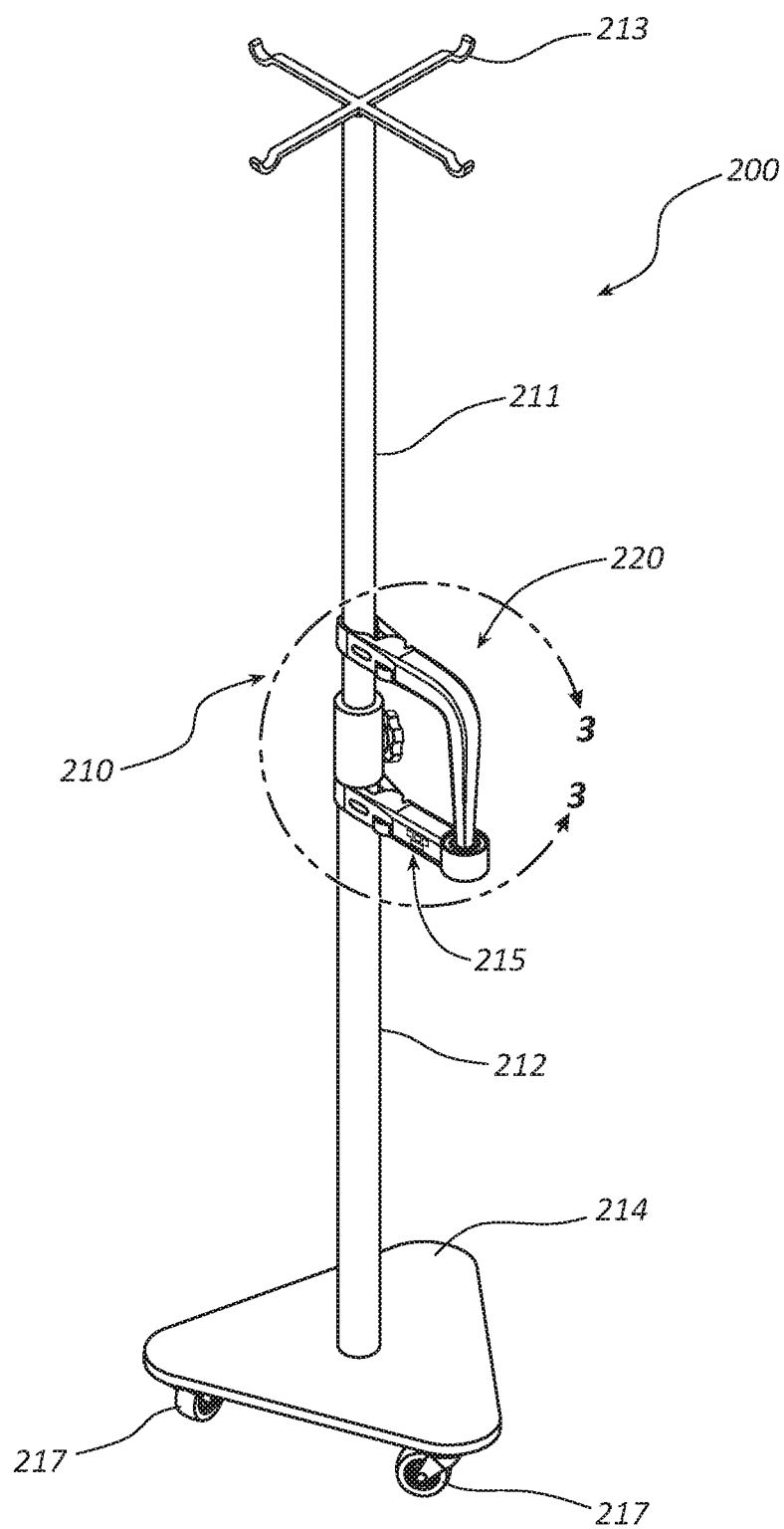
FIG. 2 is a perspective view of another embodiment of a UV disinfecting device coupled to an IV pole.
Figure 3:
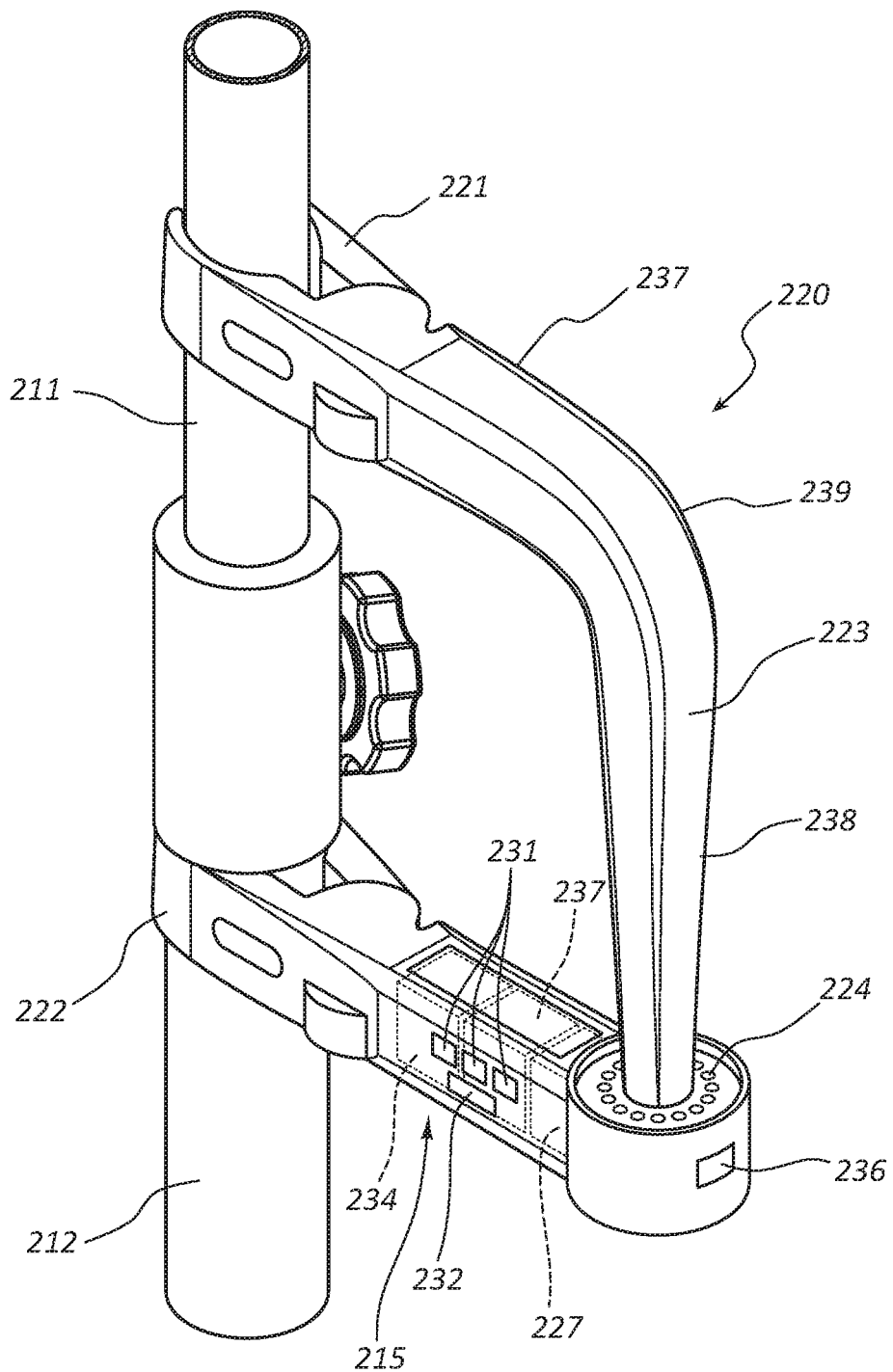
FIG. 3 is a perspective view of the UV disinfecting device of FIG. 2.

FIGS. 2-3 depict an embodiment of a UV disinfecting device 200 that resembles the UV disinfecting device 100 described above in certain respects. Accordingly, like features are designated with like reference numerals, with the leading digit incremented to "2." For example, the embodiment depicted in FIGS. 2-3 includes an IV pole 210 that may, in some respects, resemble the IV pole 110 of FIG. 1. Relevant disclosure set forth above regarding similarly identified features thus may not be repeated hereafter. Moreover, specific features of the UV disinfecting device 200 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the UV disinfecting device 200 and related components depicted in FIGS. 2-3. Any suitable combination of the features, and variations of the same, described with respect to the UV disinfecting device 100 and related components illustrated in FIG. 1 can be employed with the UV disinfecting device 200 and related components of FIGS. 2-3, and vice versa. This pattern of disclosure applies equally to further embodiments depicted in subsequent figures and described hereafter, wherein the leading digits may be further incremented.

FIGS. 2-3 are views of an embodiment of a UV disinfecting device 200. As shown, the UV disinfecting device 200 includes an IV pole 210 and a handle 220. The IV pole 210 may include an upper tube 211, a lower tube 212, a base 214, and a support 213. The upper tube 211 may be configured to telescopingly slide within the lower tube 112 to adjust a height of the IV pole 210. The lower tube 212 may be fixedly coupled to the base 214 such that the lower tube 212 extends orthogonally upward from the base 214.

The support 213 may be fixedly coupled to an upper end of the upper tube 211. The base 214 may comprise wheels or castors 217 such that the IV pole 210 may be easily moved by a patient or healthcare worker. The upper tube 211 and the lower tube 212 may be formed from various materials such as stainless steel, aluminum, polycarbonate, reinforced nylon, etc.

In some embodiments, the upper tube 211 and the lower tube 212 may comprise an antimicrobial, antifungal, and/or antiviral compound. The compound may be incorporated into the material used to form the upper and lower tubes 211, 212, or the compound may be applied to an outer surface as a coating or frosting. In some embodiments, the compound is in a concentration of from 1% to 4%. The compound may comprise agents such as ionic silver; zinc, copper; phenolic biocides; thiabendazole; quaternary ammonium compounds, including quaternary ammonium chlorides such as N,N-didecyl, N,N-diethyl ammonium chloride, and aromatic moieties (Benzalkonium chloride) such as N-decyl-N-benzyl-N,N-dimethylammonium chloride; and so forth. These compounds may be utilized individually or in any combination to enhance antimicrobial properties of the IV pole 210.

The handle 220 may be configured to provide a graspable surface and to prevent the patient and healthcare worker from grasping and contaminating the IV pole 210 when moving the UV disinfecting device 200. As shown in the embodiment of FIGS. 2-3, the handle 220 includes an upper clamp 221, a lower clamp 222, a grip 223, a UVC light emitting member 224, and a controller 215. The upper and lower clamps 221, 222 may be configured to releasably couple the handle 220 to the upper tube 211 and/or the lower tube 212. The upper and lower clamps 221, 222 may be of any suitable configuration, such as an IV pole clamp, C-clamp, quick release clamp, ratchet clamp, clamping collar, etc.

In the illustrated embodiment, the grip 223 includes a substantially horizontal portion 237 and a substantially vertical portion 238 with an arcuate portion 239 disposed between the horizontal portion 237 and the vertical portion 238. The horizontal portion 237 is coupled to the upper clamp 221 and the vertical portion 238 extends downward to couple to the UVC light emitting member 224. In other embodiments, the horizontal portion 237 may be coupled to the lower clamp 222 with the vertical portion 238 extending upward. The vertical portion 238 may taper radially outward as the vertical portion 238 extends toward the arcuate portion 239. The taper angle may range from 0 degrees to 30 degrees, from 5 degrees to 20 degrees, or from 10 degrees to 15 degrees. In the illustrated embodiment, the UVC light emitting member 224 is disposed at a lower end of the vertical portion 238 of the grip 223 within the brace 234. The UVC light emitting member 224 may include a variety of sources, including a plurality of UVC light LEDs or diodes, a mercury-based lamp, or a pulsed-xenon lamp. The UVC light emitting member 224 is configured to disperse UVC light toward the tapered surface of the vertical portion 238. The taper of the vertical portion 238 may thus be configured to facilitate exposure of the entire outer surface of the vertical portion 238 to UVC light from the UVC light emitting member 224, as the taper tends to expose the surface of the vertical portion 238 to light emitted from the lower end of the vertical portion 238.

Photobiocidal nanoparticles may be coated or frosted on the outer surface of the vertical portion 238. The photobiocidal nanoparticles may comprise titanium dioxide, silica dioxide, zinc dioxide, or other photobiocidal materials. The photobiocidal nanoparticles may be activated by UVC light from the UVC light emitting member 224. The photobiocidal nanoparticles may be configured to enhance the disinfecting properties of the UV disinfecting device 200.

With continued reference to FIGS. 2-3, in the depicted embodiment, the controller 215 is disposed within the brace 234. The controller 215 may include a power supply 232, a processor 227, and an infrared proximity sensor 236. The power supply 232 may comprise rechargeable batteries. Alternatively or additionally, a power cord from an electrical outlet or other electrical power source may be plugged into the power supply 232 to recharge the batteries and may be unplugged from the power supply 232 when the UV disinfecting device 200 is moved. The processor 227 may be coupled to the UVC light emitting member 224 and may be configured to control duty cycles of the UVC light emitting member 224. For example, the processor 227 may control the frequency, duration, and intensity at which the UVC light emitting member 224 produces UVC light. The proximity sensor 236 may be coupled to the processor 227 and may be configured to sense the proximity of the patient or the healthcare worker. A signal may be sent to the processor 227 when the patient or healthcare worker is proximate to the UV disinfecting device 200, such that the UV light emitting member 224 is turned off or not permitted to start emitting UVC light. The controller 215 may comprise LED lights 231 to visibly indicate the status of the controller 215, such as on, off, charging, low battery, etc.

In use, the UV disinfecting device 200 may be used in a healthcare setting to hang medicaments from the support 213 when providing medical treatment to the patient. The handle 220 may be grasped by the patient or healthcare worker to move the UV disinfecting device 200 to an acceptable location. Grasping of the handle 220 may tend to contaminate the outer surface of the vertical portion 238 with pathogenic microorganisms. Thus, following the patient treatment, the UV disinfecting device 200 may be disinfected. The processor 227 may be configured to turn on the UVC light emitting member 224 after use by a patient. The UVC light emitting member 224 may then disperse the UVC light toward the outer surface of the vertical portion 238 to kill or disable the microorganisms disposed on outer surface of the vertical portion 238. The UVC light may also activate the photobiocidal nanoparticles to enhance the killing or disabling of the microorganisms.

Figure 4:
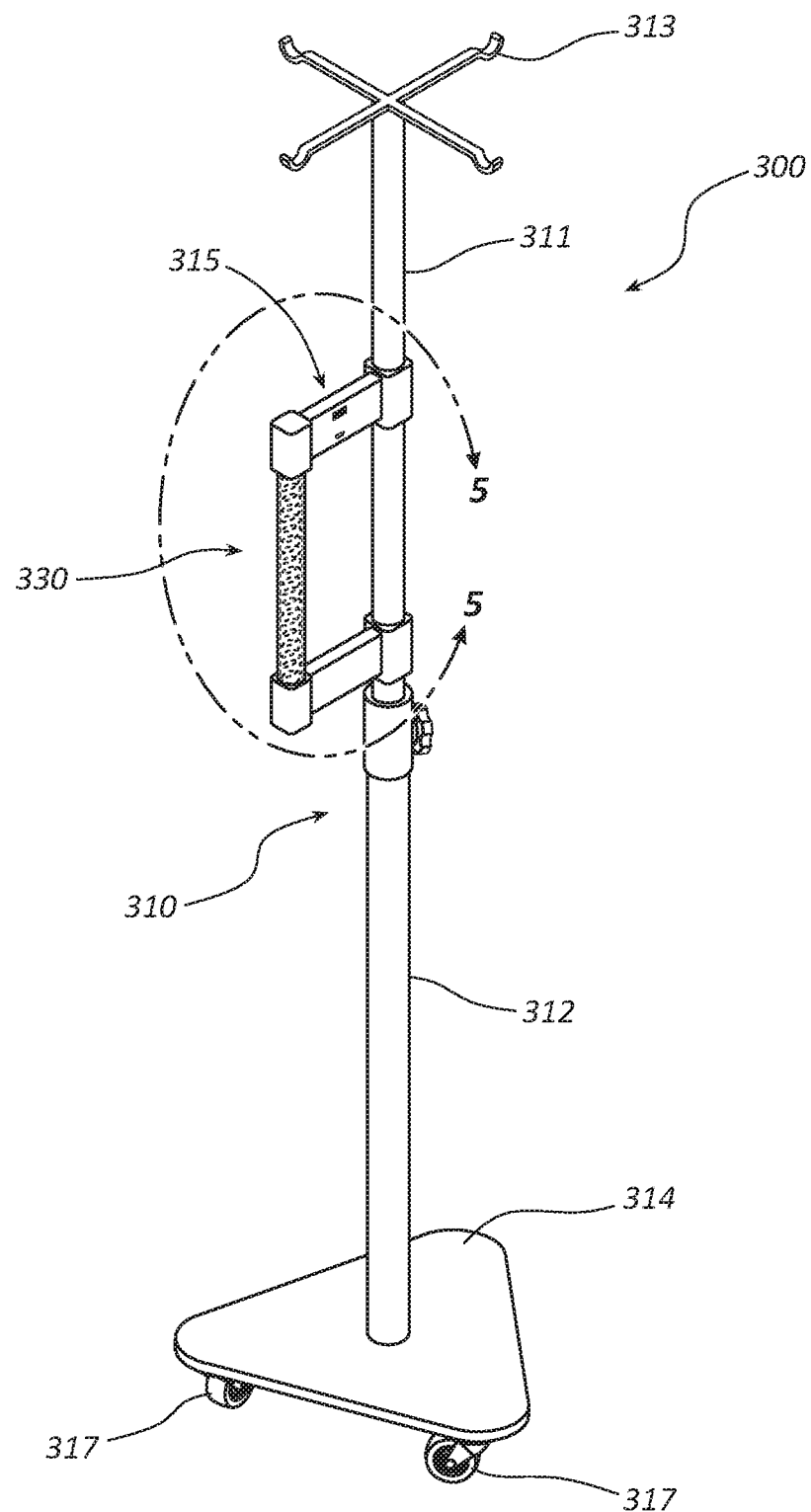
FIG. 4 is a perspective view of another embodiment of a UV disinfecting device coupled to an IV pole.
Figure 5:
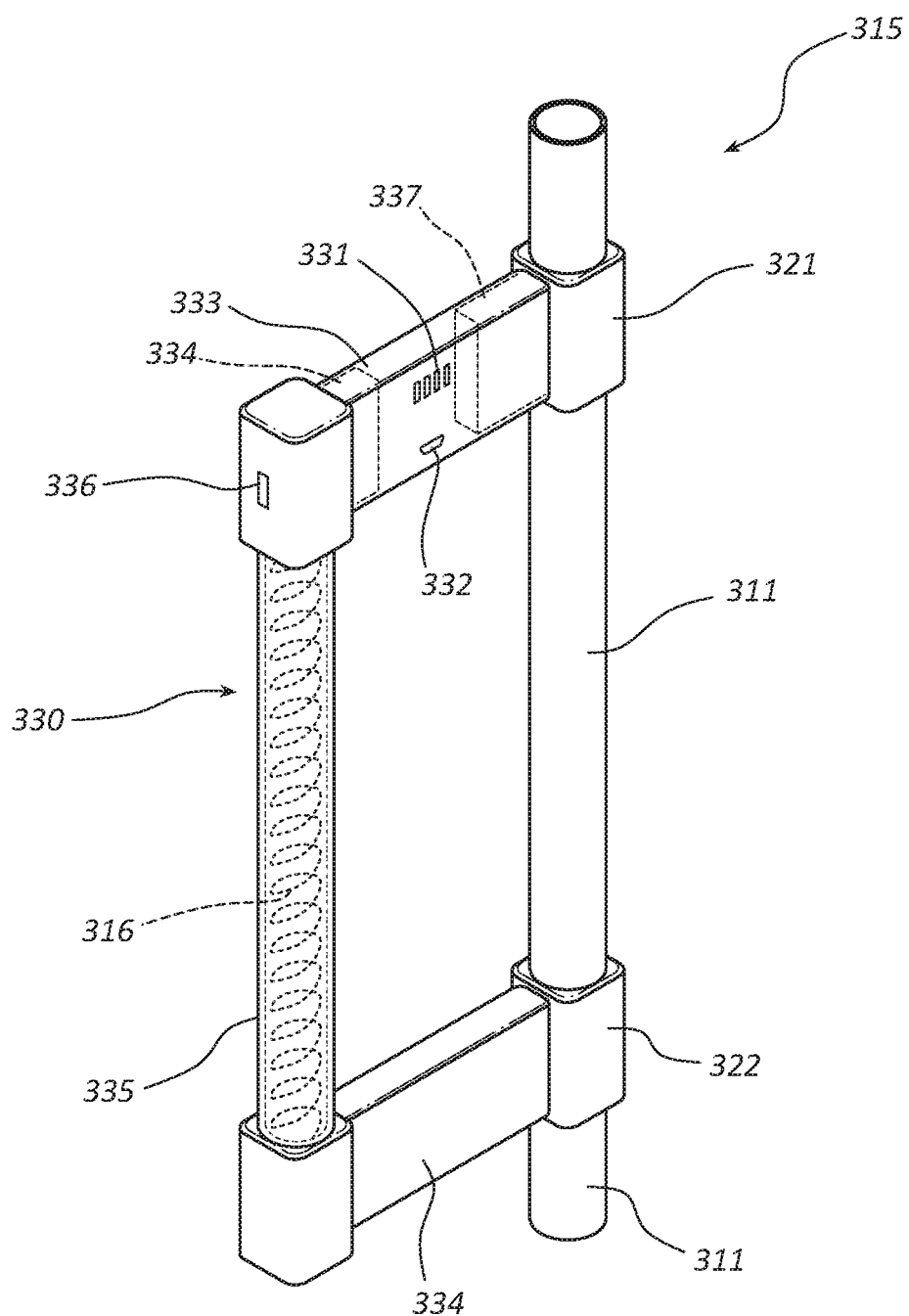
FIG. 5 is a perspective view of the UV disinfecting device of FIG. 4.

FIGS. 4-5 are a view of an embodiment of a UV disinfecting device 300. As shown, the UV disinfecting device 300 includes an IV pole 310 and a handle 330. The IV pole 310 may include an upper tube 311, a lower tube 312, a base 314, and a support 313. The upper tube 311 may be configured to telescopingly slide within the lower tube 312 to adjust a height of the IV pole 310. The lower tube 312 may be fixedly coupled to the base 314 such that the lower tube 312 extends orthogonally upward from the base 314. The support 313 may be fixedly coupled to an upper end of the upper tube 311. The base 314 may comprise wheels or castors 317 such that the IV pole 310 may be easily moved by the patient or healthcare worker. The upper tube 311 and the lower tube 312 may be formed from various materials such as stainless steel, aluminum, polycarbonate, reinforced nylon, etc.

In some embodiments, the upper tube 311 and the lower tube 312 may comprise an antimicrobial, antifungal, and/or antiviral compound. The compound may be incorporated into the material used to form the upper and lower tubes 311, 312, or the compound may be applied to an outer surface as a coating or frosting. The compound may be in a concentration of from 1% to 4%. The compound may comprise agents such as ionic silver; zinc; copper; phenolic biocides; thiabendazole; quaternary ammonium compounds, including quaternary ammonium chlorides such as N,N-di-decyl-N,N-diethyl ammonium chloride, and aromatic moieties (Benzalkonium chloride) such as N-decyl-N-benzyl-N,N-dimethylammonium chloride; and so forth. These compounds may be utilized individually or in any combination to enhance antimicrobial properties of the IV pole 310.

The handle 330 may be configured to provide a graspable to avoid instances where patient and/or healthcare worker directly grasp (and thus potentially contaminate) the IV pole 310 when moving the IV pole 310. The handle 330 may include an upper clamp 321, a lower clamp 322, a grip 335, a lower brace 334, an upper brace 333, a UV light transmitting member 316, and a controller 315. The upper and lower clamps 321, 322 may be configured to releasably couple the handle 330 to the upper tube 311 and/or the lower tube 312. In another embodiment, the upper and lower clamps may be fixedly coupled to the upper tube 311 and/or the lower tube 312. The upper and lower clamps 321, 322 may be of any suitable configuration, such as an IV pole clamp, C-clamp, quick release clamp, ratchet clamp, clamping collar, etc. In the illustrated configuration, the upper and lower clamps 321, 322 are coupled to the upper and lower braces 333, 334, respectively.

As illustrated in FIGS. 4-5, the grip 335 is substantially vertically coupled to and disposed between the upper and lower braces 333, 334. In other embodiments within the scope of this disclosure, the grip 335 may be disposed at other angles. The grip 335 may be formed as a hollow, elongate cylinder having a circular cross-section. In some embodiments, the grip 335 may be a hollow, elongate tube having other geometric cross-sectional shapes, such as triangular square, rectangular, or other shapes. The grip 335 may be formed from a UVC light transparent material with a transmission cutoff of wavelengths of less than 200 nm, such as quartz glass. In other embodiments, the grip 335 may be formed from other glass type or polymeric materials, such as cyclic olefin copolymer, fluorinated ethylene propylene (FEP), fused silica, amorphous polymers with adequate clarity, and select semi-crystalline polymers with adequate translucence and so forth.

Photobiocidal nanoparticles may be coated or frosted on the outer surface of the grip 335. The photobiocidal nanoparticles may comprise titanium dioxide, silica dioxide, zinc dioxide, or other photobiocidal materials. The photobiocidal nanoparticles may be activated by UVC light from the UV light transmitting member 316. The photobiocidal nanoparticles may be configured to enhance the disinfecting properties of the UV disinfecting device 300.

With continued reference to FIGS. 4-5, in the depicted embodiment, the controller 315 is disposed within the upper brace 333. In other embodiments, the controller 315 may be disposed within the lower brace 334. The controller 315 may include a power supply 332, a processor 327, a UVC light emitting member 324, and an infrared proximity sensor 336. The power supply 332 may comprise rechargeable batteries. Alternatively or additionally, a power cord from an electrical outlet or other electrical power source may be plugged into the power supply 332 to recharge the batteries and may be unplugged from the power supply 332 when the UV disinfecting device 300 is moved. The processor 327 may be coupled to the UVC light emitting member 324 and may be configured to control duty cycles of the UVC light emitting member 324. For example, the processor 327 may control the frequency, duration, and intensity at which the UVC light emitting member 324 produces UVC light. The proximity sensor 336 may be coupled to the processor 327 and may be configured to sense the proximity of the patient or the healthcare worker. A signal may be sent to the processor 327 when the patient or healthcare worker is proximate to the UV disinfecting device 300, such that the UVC light emitting member 324 is turned off or not permitted to start emitting UVC light. The controller 315 may comprise LED lights 331 to visibly indicate the status of the controller 315, such as on, off, charging, low battery, etc.

The UVC light emitting member 324 may be coupled to the UV light transmitting member 316. The UVC light emitting member 324 may be configured as UVC light emitting diodes or LEDs, a mercury-based lamp, a pulsed-xenon lamp, or other sources. The UV light transmitting member 316 may comprise optical fibers or any other suitable structure configured to transmit UV light and more particularly, UVC light. The UV light transmitting member 316 may be disposed within the grip 335. The UV light transmitting member 316 may be disposed in a spiral configuration to increase the length of the UV light transmitting member 316 disposed within the grip 335. In other embodiments, the UV light transmitting member 316 may be straight or divided into a plurality of strands.

In use, the UV disinfecting device 300 may be used in a healthcare setting to hang medicaments from the support 313 when providing medical treatment to the patient. The handle 330 may be grasped by the patient or healthcare worker to move the UV disinfecting device 300 to an acceptable location. Grasping of the handle 330 of the UV disinfecting device 300 may contaminate the outer surface of the grip 335 with pathogenic microorganisms. Following the patient treatment, the UV disinfecting device 300 may be disinfected. The controller 315 can emit UVC light to the UV light transmitting member 316 and the UV light transmitting member 316 may transmit the UVC light through the wall of the grip 335. The UVC light may kill or disable the microorganisms disposed on the outer surface of the grip 335. The UVC light may also activate the photobiocidal nanoparticles to enhance the killing or disabling of the microorganisms.

Figure 6:
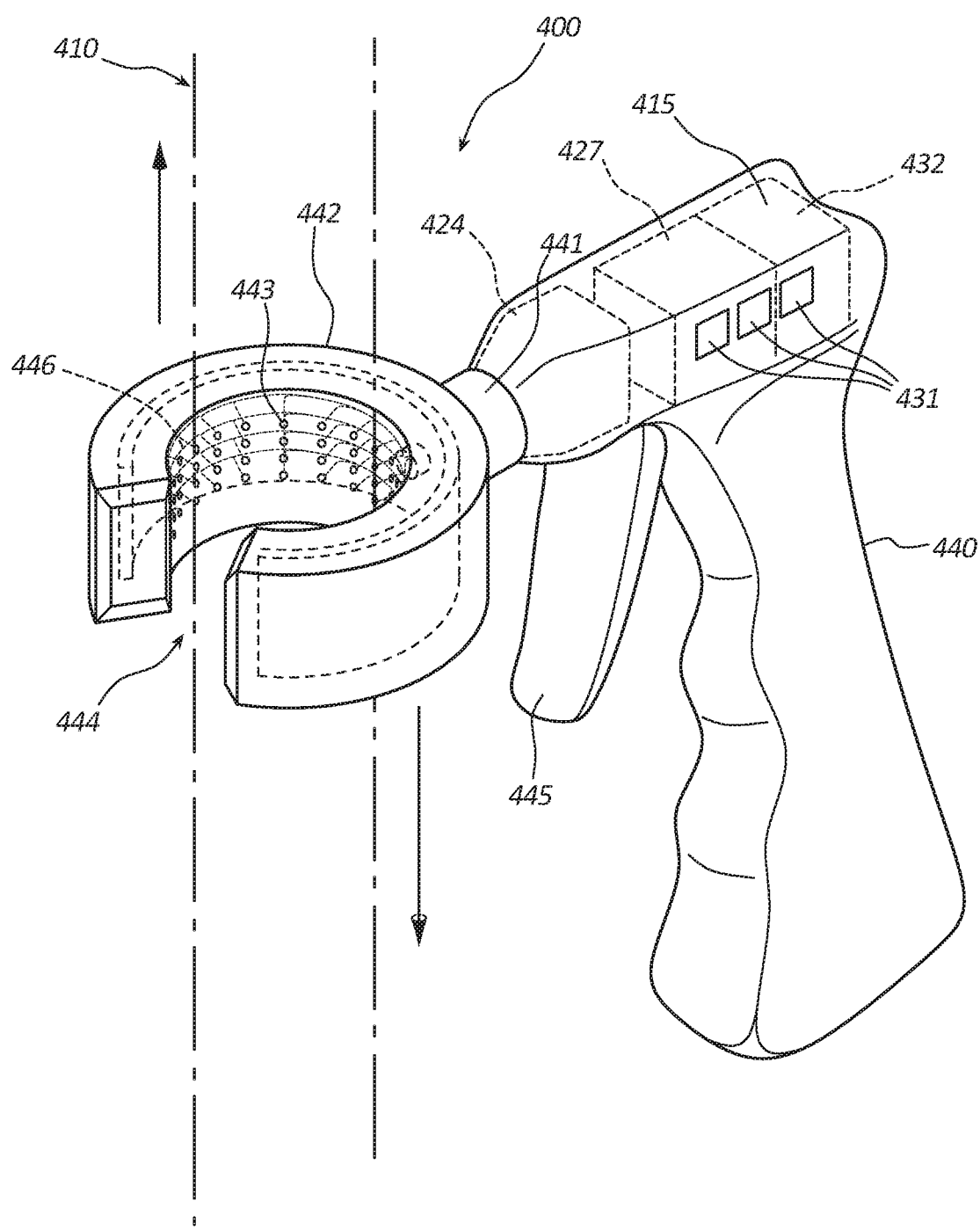
FIG. 6 is a perspective view of an embodiment of another UV disinfecting device.

FIG. 6 shows an embodiment of a handheld UV disinfecting device 400. The UV disinfecting device 400 includes a handle 440, a controller 415, a connector 441, and a UV dispensing member 442. The handle 440 is configured to be grasped by a hand of the healthcare worker. The handle 440 may include grip enhancing features, such as bumps, ridges, grooves, surface texturing, soft material, and so forth. The handle 440 is coupled to and may extend downward from the controller 415. The connector 441 is disposed between the controller 415 and the UV dispensing member 442.

The controller 415 includes a power supply 432, a processor 427, a UVC light emitting member 424, and a trigger 445. The power supply 432 may comprise rechargeable batteries. Alternatively or additionally, a power cord from an electrical outlet or other electrical power source may be plugged into the power supply 432 to recharge the batteries and may be unplugged from the power supply 432 when the UV disinfecting device 400 is in use. The processor 427 may be coupled to the UVC light emitting member 424 and may be configured to control activation and duty cycles of the UVC light emitting member 424. For example, the processor 427 may control the frequency, duration, and intensity at which the UVC light emitting member 424 produces UVC light. The trigger 445 may be coupled to the controller 415 and to the handle 440. The trigger 445 may be configured to function as a switch to signal the processor 427 to activate the UVC light emitting member 424. The controller 415 may comprise LED lights 431 to visibly indicate the status of the controller 415, such as on, off, charging, low battery, etc.

As illustrated in FIGS. 5-6, the UV dispensing member 442 is coupled to the connector 441. The UV dispensing member 442 of the illustrated embodiment is substantially C-shape with an opening 444 disposed away from the handle 440. The opening 444 is sized to allow for passage of an IV pole 410 through the opening 444 and into an interior of the UV dispensing member 442. A plurality of ports 443 are disposed on an interior surface. Ends of optical fibers 446 may be disposed within the ports 443. The optical fibers 446 may be coupled to the UVC light emitting member 424 and may be configured to transmit UVC light.

In use, the UV disinfecting device 400 may be used in a healthcare setting to disinfect the IV pole 410 and other medical appliances that are used in a treatment of the patient. During the use, an outer surface of the IV pole 410 may be contaminated with pathogenic microorganisms. The handle 440 of the UV disinfecting device 400 may be grasped by the healthcare worker to move the UV disinfecting device 400 adjacent to the IV pole 410. The UV dispensing member 442 may be positioned around the IV pole 410 by moving the UV disinfecting device 400 horizontally such that the IV pole 410 passes through the opening 444 and into the interior of the UV dispensing member 442. The trigger 445 may be displaced toward the handle 440 to activate the UVC light emitting member 424. The UVC light may be emitted from the UVC light emitting member 424 to the optical fibers 446 and may be dispersed from the ends of the optical fibers 446 disposed within the ports 443 toward the outer surface of the IV pole 410. The UV disinfecting device 400 may be moved up and down along a longitudinal axis of the IV pole 410 such that the outer surface of the IV pole 410 is exposed to the UVC light and the microorganisms on the outer surface may be killed or disabled.

Figure 7:
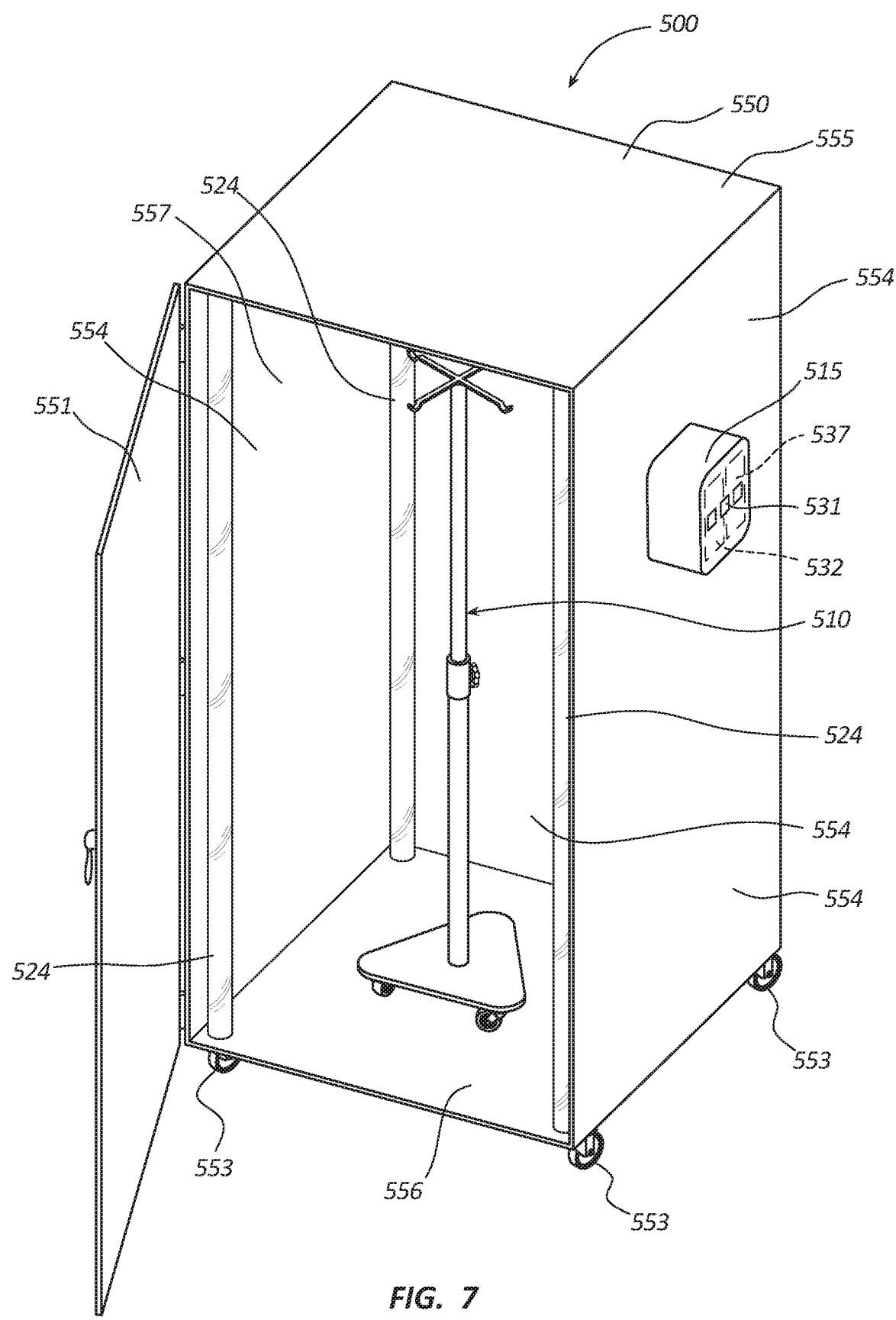
FIG. 7 is a perspective view of another embodiment of a UV disinfecting device.

FIG. 7 shows an embodiment of a UV disinfecting device 500 comprising a cabinet 550, a controller 515, and UVC light emitting members 524. The cabinet 550 is configured to enclose an IV pole 510 during a UV disinfection process. The cabinet 550 as illustrated in FIG. 7 comprises a plurality of walls 554, a ceiling 555, a floor 556, a door 551, and a plurality of wheels or castors 553. The cabinet 550 has a square shape. In other embodiments the cabinet 550 may be of any shape, such as rectangular, circular, polygonal etc. The height of the cabinet 550 may be sized to accommodate the IV pole 510 in an upright orientation. The walls 554, ceiling 555, floor 556, and door 551 may be formed of various materials configured to block UVC light, such as metals (including steel, stainless steel, and aluminum), press board, thermoset material sheets (including urethane, phenolic, urea, high molecular weight polyoxymethylene), etc. In another embodiment, the walls 554, ceiling 555, and door 551 may be configured as curtains and formed of any suitable flexible material that is capable of blocking UVC light, such as woven or non-woven synthetic or natural materials, reflective mylar, thermoset polymers including urethane, silicone, neoprene, vinyl, etc. In certain embodiments, the cabinet 550 may comprise a combination of rigid and flexible walls 554. For example, side and back walls 554 can be rigid and a door 551 can be flexible. The door 551 may be hinged on one side and may comprise a latch to secure the door 551 in a closed state. The wheels or castors 553 may be coupled to the floor 556 to facilitate easy movement of the cabinet 550 to a desired location.

An inside surface 557 of the walls 554, the ceiling 555, the floor 556, and the door 551 may be configured to reflect UVC light emitted by the UVC light emitting members 524 disposed within the cabinet 550. The inside surface 557 may be integral to the walls 554 or may be a coating on the walls 554. The inside surface 557 may be smooth or may comprise a plurality of facets configured to reflect the UVC light in a plurality of directions.

As illustrated in FIG. 7, the controller 515 is disposed on a wall 554 of the cabinet 550. The controller 515 may comprise a power supply 532 and a processor 527. The power supply 532 may be coupled to a power cord configured to be plugged into an power outlet. The power supply 532 may be coupled to the processor 527 and to the UVC light emitting members 524. The processor 527 may be coupled to the UVC light emitting members 524 and may be configured to control activation and duty cycles of the UVC light emitting members 524. For example, the processor 527 may control the frequency, duration, and intensity at which the UVC light emitting members 524 produce UVC light. The controller 515 may comprise LED lights 531 to visibly indicate the status of the controller 515, such as on, off, etc. The processor 527 may be coupled to a switch configured to turn off the UVC light emitting members 524 when the door 551 is opened during the disinfecting process.

The UVC light emitting members 524 are disposed within the cabinet 550. The UVC light emitting member 524 is positioned in each of four corners of the cabinet 550 to maximize exposure of the IV pole 510 to UVC light. In other embodiments, the UVC light emitting members 524, may be disposed in any suitable location within the cabinet 550, such as in the middle of a wall 554, on the ceiling 555, on the floor 556, etc.

In use, the UV disinfecting device 500 may be moved to a desired location and a power cord plugged into a wall power outlet. A medical appliance, such as the IV pole 510, may be placed into the cabinet 550. The door 551 may be closed. The processor 527 may activate the UVC light emitting members 524 to initiate the disinfection process. The processor 527 may control the duration and intensity of UVC light emitted from the UVC light emitting members 524. LED lights 531 on the controller 515 may indicate the status of the disinfection process. If the door 551 is opened prior to the completion of the disinfection process, the processor 527 may turn off power to the UVC light emitting members 524 until the door is closed.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially horizontal" is recited with respect to a feature, it is understood that in further embodiments, the feature can have a precisely horizontal configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A disinfecting device for an elongate medical appliance, the disinfecting device comprising:
   an ultraviolet C (UVC) light transmitting member configured to irradiate an outer surface of the elongate medical appliance with UVC light; and
   a handle comprising:
      a first clamp;
      a second clamp; and
      a grip,
   wherein the UVC light transmitting member is configured to be coupled to the elongate medical appliance.

2. The disinfecting device of claim 1, further comprising:
   a power supply;
   a UVC light emitting member coupled to the UVC light transmitting member; and
   a proximity sensor.

3. The disinfecting device of claim 1, wherein the grip comprises a hollow cylinder formed from UVC light transparent material, wherein the UVC light transmitting member is disposed within the grip.

4. The disinfecting device of claim 1, wherein the UVC light emitting member is disposed adjacent an end of the grip.

5. The disinfecting device of claim 4, wherein a diameter of a first end of the grip adjacent the UVC light transmitting member is smaller than a diameter of a second end of the grip.

6. The disinfecting device of claim 1, wherein an outer surface of the grip is frosted with photobiocidal nanoparticles.

7. A system to disinfect an elongate medical appliance, the system comprising:
   an elongate medical appliance that comprises a hollow cylinder formed from a UVC light transparent material;
   an ultraviolet C (UVC) light transmitting member coupled to the elongate medical appliance;
   a power supply;
   a UVC light emitting member coupled to the UVC light transmitting member; and
   a proximity sensor configured to terminate emission of the UVC light when a healthcare worker and/or patient is adjacent the elongate medical appliance,
   wherein the UVC light transmitting member is disposed within the elongate medical appliance.

8. The system of claim 7, wherein the elongate medical appliance further comprises an IV pole.

9. The system of claim 7, wherein the UVC light transparent material is quartz glass.

10. The system of claim 7, wherein the elongate medical appliance further comprises a frosting of photobiocidal nanoparticles on an outer surface of the elongate member.

11. The system of claim 10, wherein the photobiocidal nanoparticles comprise titanium dioxide.

12. The system of claim 7, wherein the UVC light emitting member is coupled to the UVC light transmitting member.

13. A disinfecting device for an elongate medical appliance, the disinfecting device comprising:
   a handheld member with a handle;
   an ultraviolet C (UVC) dispensing member coupled to the handheld member, the ultraviolet C (UVC) dispensing member comprising a C-shape and an opening disposed away from the handheld member;
   a plurality of ports disposed on an inner surface of the ultraviolet C (UVC) dispensing member; and
   a UVC light emitting member disposed within the handle and coupled to the ultraviolet C (UVC) dispensing member;
   wherein the ultraviolet C (UVC) dispensing member is configured to be coupled to the elongate medical appliance through the opening and at least partially surround the elongate medical appliance is movable along a longitudinal axis of the elongate medical appliance, and
   wherein an outer surface of the elongate medical appliance is exposed to UVC light from the UVC light emitting member through the plurality of ports.

* * * * *